(12) United States Patent
Bialecki et al.

(10) Patent No.: US 7,658,725 B2
(45) Date of Patent: Feb. 9, 2010

(54) ENCLOSED NEEDLE DEVICE WITH DUCKBILL RELEASE MECHANISM

(75) Inventors: Dennis M Bialecki, Oxford, CT (US); Nhut M Diep, Hartford, CT (US); Alan D King, Burlington, CT (US); Thomas T Koehler, Simsbury, CT (US)

(73) Assignee: Smiths Medical ASD, Inc., Rockland, MA (US)

( * ) Notice: Subject to any disclaimer, the term of this patent is extended or adjusted under 35 U.S.C. 154(b) by 974 days.

(21) Appl. No.: 11/276,152

(22) Filed: Feb. 16, 2006

(65) Prior Publication Data

US 2007/0191776 A1 Aug. 16, 2007

(51) Int. Cl.
A61M 5/178 (2006.01)

(52) U.S. Cl. .................................. 604/164.08

(58) Field of Classification Search .................. 604/110, 604/158, 162, 164.01–164.08
See application file for complete search history.

(56) References Cited

U.S. PATENT DOCUMENTS

| | | | |
|---|---|---|---|
| 4,747,831 A | 5/1988 | Kulli | |
| 4,762,516 A | 8/1988 | Luther et al. | |
| 4,778,453 A | 10/1988 | Lopez | |
| 4,832,696 A | 5/1989 | Luther et al. | |
| 4,834,718 A | 5/1989 | McDonald | |
| 4,846,805 A | 7/1989 | Sitar | |
| 4,929,241 A | 5/1990 | Kulli | |
| 4,944,725 A | 7/1990 | McDonald | |
| 4,944,728 A | 7/1990 | Carrell et al. | |
| 4,950,252 A | 8/1990 | Luther et al. | |
| 5,000,740 A | 3/1991 | Ducharme et al. | |
| 5,108,379 A | 4/1992 | Dolgin et al. | |
| 5,135,504 A | 8/1992 | McLees | |
| 5,156,599 A | 10/1992 | Ranford et al. | |
| 5,205,829 A | 4/1993 | Lituchy | |
| 5,215,525 A | 6/1993 | Sturman | |

(Continued)

FOREIGN PATENT DOCUMENTS

CA 2033361 11/2003

(Continued)

OTHER PUBLICATIONS

International Search Report and Written Opinion for PCT/US2007/062185, mailed on Jul. 4, 2007 (17 pages).

*Primary Examiner*—Nicholas D Lucchesi
*Assistant Examiner*—Aarti B Berdichevsky
(74) *Attorney, Agent, or Firm*—Wood, Herron & Evans, LLP (57) ABSTRACT

An enclosed needle catheter insertion device (10) includes a catheter (12) and a needle insertion device (14) which are held together by cooperating arms (52, 53) with one or more detents (56) cooperating with a radially projecting surface (26) of the catheter hub (16). Insertion device (14) includes a guard housing (30) to enclose a needle (34) in a shielded position and a support housing (32) supporting the needle (34) for movement between a ready position, with the tip (36) of the needle (34) exposed, to the shielded position. Cooperating lock elements (47, 78) are provided for the housings (30, 32) which are positioned to define a lock actuation stage between the ready and shielded positions, whereat the needle is still within a passageway (54) defined by the cooperating arms (52, 53).

34 Claims, 5 Drawing Sheets

U.S. PATENT DOCUMENTS

| | | |
|---|---|---|
| 5,215,528 A | 6/1993 | Purdy et al. |
| RE34,416 E | 10/1993 | Lemieux |
| 5,300,045 A | 4/1994 | Plassche, Jr. |
| 5,322,517 A | 6/1994 | Sircom et al. |
| 5,328,482 A | 7/1994 | Sircom et al. |
| 5,334,158 A | 8/1994 | McLees |
| 5,344,408 A | 9/1994 | Partika |
| 5,409,461 A | 4/1995 | Steinman |
| 5,419,766 A | 5/1995 | Chang et al. |
| 5,423,766 A | 6/1995 | Di Cesare |
| 5,533,974 A | 7/1996 | Gaba |
| 5,558,651 A | 9/1996 | Crawford et al. |
| 5,599,310 A | 2/1997 | Bogert |
| 5,601,532 A | 2/1997 | Gaba |
| 5,601,536 A | 2/1997 | Crawford et al. |
| 5,611,781 A | 3/1997 | Sircom et al. |
| 5,662,610 A | 9/1997 | Sircom |
| 5,676,658 A | 10/1997 | Erskine |
| 5,690,619 A | 11/1997 | Erskine |
| 5,695,474 A | 12/1997 | Daugherty |
| 5,697,907 A | 12/1997 | Gaba |
| 5,800,395 A | 9/1998 | Botich et al. |
| 5,830,189 A | 11/1998 | Chang |
| 5,879,337 A | 3/1999 | Kuracina et al. |
| 5,911,705 A | 6/1999 | Howell |
| 6,004,294 A | 12/1999 | Brimhall et al. |
| 6,203,527 B1 | 3/2001 | Zadini et al. |
| 6,221,047 B1 | 4/2001 | Greene et al. |
| 6,280,419 B1 | 8/2001 | Vojtasek |
| 6,379,333 B1 | 4/2002 | Brimhall et al. |
| 6,443,929 B1 | 9/2002 | Kuracina et al. |
| 6,582,402 B1 | 6/2003 | Erskine |
| 6,595,954 B1 | 7/2003 | Luther et al. |
| 6,595,955 B2 | 7/2003 | Ferguson et al. |
| 6,623,458 B2 | 9/2003 | Woehr et al. |
| 6,629,957 B1 | 10/2003 | Wiklund |
| 6,629,959 B2 | 10/2003 | Kuracina et al. |
| 6,652,490 B2 | 11/2003 | Howell |
| 6,689,102 B2 | 2/2004 | Greene |
| 6,695,814 B2 | 2/2004 | Greene |
| 6,749,588 B1 | 6/2004 | Howell et al. |
| 6,796,962 B2 | 9/2004 | Ferguson et al. |
| 6,860,871 B2 | 3/2005 | Kuracina et al. |
| 6,902,546 B2 | 6/2005 | Ferguson |
| 6,972,002 B2 | 12/2005 | Thorne |
| 2002/0169418 A1 | 11/2002 | Menzi et al. |
| 2003/0100868 A1 | 5/2003 | Ferguson et al. |
| 2003/0199827 A1 | 10/2003 | Thorne |
| 2004/0049155 A1 | 3/2004 | Schramm |
| 2004/0078003 A1 | 4/2004 | Smith et al. |
| 2004/0127854 A1 | 7/2004 | Leinsing et al. |
| 2004/0186434 A1 | 9/2004 | Harding et al. |
| 2004/0204681 A1 | 10/2004 | Thoresen et al. |
| 2004/0236288 A1 | 11/2004 | Howell |
| 2004/0267204 A1 | 12/2004 | Bristowicz |
| 2005/0038384 A1 | 2/2005 | Li |
| 2005/0096592 A1 | 5/2005 | Carlyon et al. |
| 2005/0113755 A1 | 5/2005 | Greene et al. |
| 2005/0277879 A1 | 12/2005 | Daga |

FOREIGN PATENT DOCUMENTS

| | | |
|---|---|---|
| EP | 0747085 A2 | 11/1996 |
| EP | 0750916 | 1/1997 |
| JP | 1995024071 | 1/1995 |
| JP | 2001190683 | 7/2001 |
| JP | 2004154364 | 6/2004 |
| WO | 0168174 A2 | 9/2001 |

ENCLOSED NEEDLE DEVICE WITH DUCKBILL RELEASE MECHANISM

FIELD OF THE INVENTION

The present invention relates to enclosed needle devices, and more particularly to release mechanisms for selectively holding the enclosed needle device to a catheter hub.

DESCRIPTION OF PRIOR ART

Over-the-needle catheters are well known in the art. In such devices, a needle projects through a catheter tube with its sharp tip projecting out of the end of the tube. The sharp tip of the needle is used to pierce the skin and the blood vessel so as to carry the end of the catheter into the vessel. Once the catheter is in place, the needle is withdrawn leaving the catheter hub exposed for use such as for connection to a medical fluid line or the like to administer or withdraw fluids.

In order to reduce the risks of accidental needle sticks after the needle has been removed from the catheter, various proposals have been made to shield the needle tip. One class of devices intended to shield the needle tip includes an elongated needle guard housing into which the needle is received as it is pulled out from the catheter. The guard housing may include as part of its distal end a nose similar to a male slip luer that is adapted to frictionally engage with the female luer tapered interior surface of the catheter hub such that the guard housing may be pulled free from the catheter hub. The guard housing is of sufficient length that it essentially encloses the entire length of the needle therein when the needle is pulled out of the catheter, thus shielding the needle tip. In some cases, the sharp tip is fully inside the guard housing, while in others, the sharp tip may be inside the nose to thus maintain alignment of the needle. In either setting, however, the needle is considered to be enclosed and the tip shielded. To that end, the needle is supported on a needle support hub or housing movable within the guard housing from a first or ready position at which the distal end of the support housing is positioned toward the distal end of the guard housing with the needle extending out of the nose of the guard housing (and through the catheter with the needle tip exposed when the guard housing is held to the catheter hub), to a second or shielded position with the distal end of the support housing positioned away from the distal end of the guard housing so as to withdraw the needle to be enclosed by the guard housing.

The support housing might be spring biased to automatically move the needle into the second position when a latch is activated as shown, for example, in U.S. Pat. No. 4,747,831 and in the commercially available AutoGuard shielded IV catheter from Becton Dickinson and Company. Or the support housing may be manually moved to the second position such as by manipulation of walls or wings of or attached to the support housing. In the manual type of device, a locking structure, such as a projection and slot detent mechanism on the housings, cooperate to retain the housings with the needle in the second position enclosed in the guard housing thus shielding the needle tip and so that the needle support can not readily be manipulated to project the needle tip back out of the guard housing. An example of such a manual device is the highly successful PROTECTIV Safety I.V. Catheter marketed by Medex, Inc., the assignee hereof. After moving into the second, shielded position of the needle, the guard housing may be pulled from the catheter hub and discarded with the needle shielded therein, leaving the catheter hub accessible as necessary.

SUMMARY OF THE INVENTION

While devices that use an elongated housing to shield the needle tip by enclosing the needle have been well-accepted and are in widespread use, further improvements are desired. By way of example, the guard housing is held to the catheter hub by friction alone, such that it is possible to disengage the components with the needle tip still exposed. Further, it is often desirable to be able to rotate the catheter hub relative to the guard housing to thread the catheter tube into the patient. The friction fit of the nose to the catheter hub to hold the guard housing to the hub limits the ability to achieve such rotation while keeping the components held together. Moreover, with the catheter in place, overcoming the friction fit to remove the shielded needle from the catheter hub after withdrawal of the needle into the guard housing may result in undesired movement or withdrawal of the catheter tube.

Duckbill release mechanisms have been proposed for other types of catheter insertion devices, and it is believed such mechanisms can be advantageously applied to enclosed needle devices as well. Such duckbill release mechanisms typically include a pair of cooperating members extending from a housing and sized to fit within the catheter hub. The members, which may be in the form of arms, normally define a passageway therebetween sized to slidably receive a needle shaft therethrough. One or both of the members has a holding portion, such as a radially outward detent and/or a radially inward recess, at or near its distal end to cooperate with an interior radially projecting surface, such as a radially outwardly extending recess or radially inwardly extending rib, respectively, of the catheter hub. The foregoing is referred to as a duckbill release mechanism due to the duckbill-appearance of the member(s) created by the detent and/or recess thereof.

A duckbill release mechanism is considered advantageous due to its strong hold when a needle is present and its easy release when the needle is not present. For example, when the needle is present in the passageway between the duckbill members, compression (i.e., radially inward flexing) of the members is limited such that the interface of the duckbill member holding portion and catheter hub interior radially projecting surface affords a very high holding force to keep the components together. The force required to separate the components in that circumstance, referred to as a "catheter separation force," is typically quite high as separation typically requires some deformation of the components. By contrast, when the needle is removed from the passageway, the force required to separate the components, referred to as the "catheter release force," is quite a bit lower than the catheter separation force as deformation is no longer required. Instead, one or both of the duckbill members is able to easily compress or flex toward the passageway such that a slight tug on the housing causes the duckbill(s) to yield against the catheter hub interior radially projecting surface allowing the components to be separated.

Duckbill release mechanisms have the further advantage that, depending upon the shape and positioning of the holding portion and radially projecting surface, the housing may be rotatable relative to the catheter hub, even during periods of high holding force. In the context of an enclosed needle device, the members would be defined on or at the nose of the guard housing. However, application of a duckbill release mechanism to an enclosed needle device requires more than merely providing the interfitting aspects of the nose and catheter hub. For example, in the manual type of enclosed needle device, the support and guard housings generally lock together only after the needle tip has passed within the guard housing so as to be held in a shielded state. With the addition of a duckbill release mechanism, the needle tip could pass from the duckbill passageway before the support and guard housings are locked together. Were that to occur, the catheter hub could come loose from the guard housing before the support and guard housings lock allowing the needle from the support housing to be pushed back out of the guard housing.

In the enclosed needle devices, the nature of the locking structure makes it even more likely that the components might separate before the housings are locked. In this regard, in order for the projection of the locking structure to engage the slot detent, it is necessary to go through a lock actuation stage such as where a ramp of the projection passes between and cams open a pair of fingers defined by the slot detent. The forces encountered during the lock actuation stage are typically higher than the catheter release force. Moreover, entry into the lock actuation stage exerts increased resistance against movement of the needle support housing as the fingers spread apart against the ramp. Thus, there is a risk or premature disconnection in normal use of an enclosed needle device were it to be equipped with a duckbill release mechanism.

The present invention provides a catheter release mechanism for an enclosed needle device which has the advantages of duckbill catheter hub release mechanisms, and in which the disconnection is more reliable. To that end, and in accordance with the principles of the present invention, the locking structure is arranged such that the needle support is movable into the lock actuation stage with the needle still in the duckbill passageway (and thus before the needle support moves into the shielded state), where the relatively high catheter separation force is involved. It will be appreciated that the force exerted upon entry into the lock actuation stage involves flexing of components rather than deformation thereof, such that the forces encountered upon entry into the lock actuation stage are advantageously below that of the catheter separation force. As a consequence, the forces exerted by entry into the lock actuation stage occur while the duckbill release mechanism strongly holds the guard housing and catheter hub together, thereby avoiding premature release before the lock can be engaged.

Advantageously, the locking structure is arranged such that the support housing moves through a reduced force stage to activate the lock as the needle finally comes out of the passageway. To that end, the lock projection may include a fixed or reducing width section, such as a slide wall, after the ramp such that the force exerted by the fingers thereon as the needle is continued to be pulled out of the passageway is less than the forces exerted upon entry into the lock actuation stage and/or reduces therefrom. In that way, even as the needle departs the passageway, the forces at the lock may continue to remain below the forces necessary to separate the components at the duckbill release mechanism. Once locked, the forces required to overcome the lock are extremely high, whereas the catheter release force is quite low, thus allowing the components to easily come apart after the needle has been fully enclosed with the housings locked in that state.

By virtue of the foregoing, there is thus provided a catheter release mechanism for an enclosed needle device which has the advantages of duckbill catheter hub release mechanisms, and in which the disconnection is more reliable. These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate an exemplary embodiment of the invention and, together with a general description of the invention given above, and the detailed description given below, serve to explain the invention.

DETAILED DESCRIPTION OF THE DRAWINGS

With reference to the accompanying Figures (which are not necessarily to scale in order to show the various components more readily), there is shown an exemplary embodiment 10 of an enclosed needle catheter insertion device in accordance with the principles of the present invention. Catheter insertion device 10 includes a catheter 12 and a needle insertion assembly 14 of the enclosed needle type as will become evident.

Figure 4:
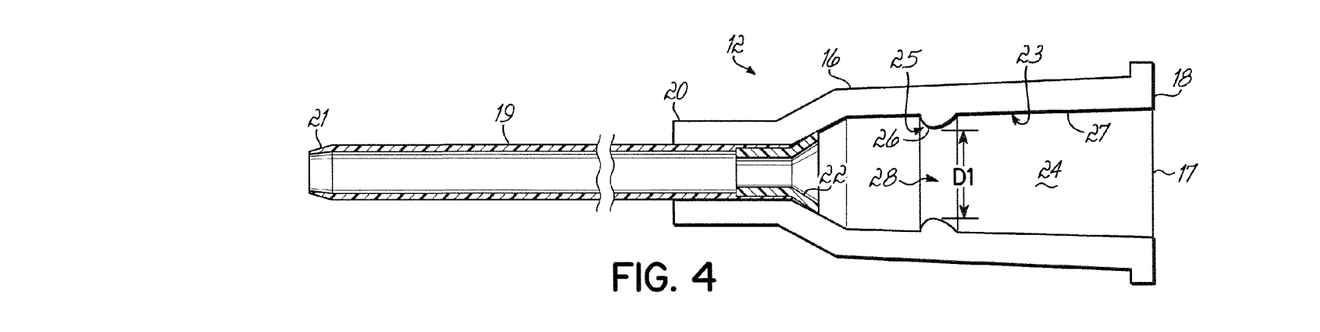
FIG. 4 is a cross-section view of the catheter of the catheter insertion device of FIG. 1.

With specific reference to FIG. 4, it can be seen that catheter 12 is comprised of a catheter hub 16 having an open mouth 17 (which, in the embodiment shown is a female luer fitting) at its proximal end 18, and catheter tube 19 extending distally from the distal end 20 of hub 16 to a beveled end 21 as is conventional. Catheter tube 19 may be secured to hub 16 in any suitable fashion, such securement being by an eyelet 22 in the embodiment 10 shown herein. Catheter hub 16 has an inner wall 23 defining the interior 24 of catheter hub 16. Associated with inner wall 23, and extending radially inwardly therefrom, is an annular rib 25 (which may be a single rib or one or more arcuate segments) to define an interior, distally-directed, radially projecting surface 26 for purposes to be explained. Proximal portion 27 of inner wall 23 extending between mouth 17 and rib 25 is tapered in accordance with luer standards to define a female luer. Rib 25 has an inwardly-most aspect 28 defining a catheter hub inner diameter D1 for purposes to be explained.

Figure 2:
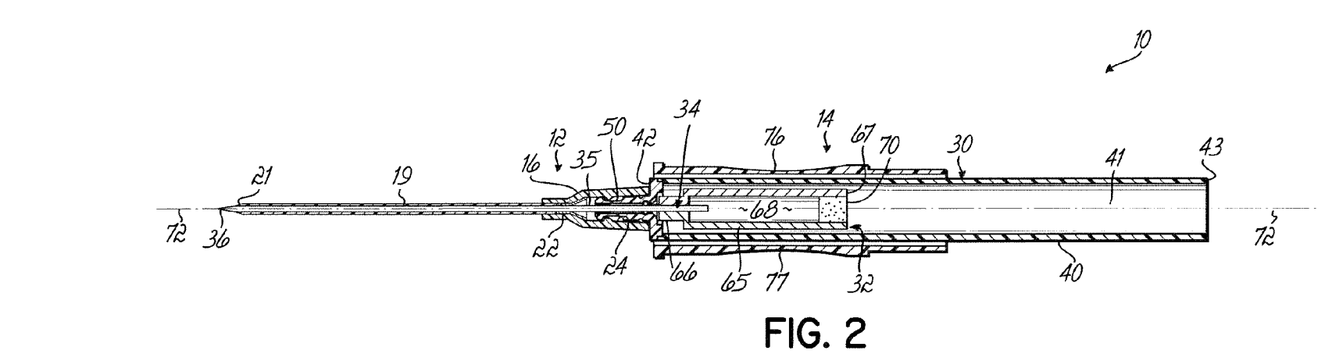
FIG. 2 is a cross-section view along line 2-2 of FIG. 1.

With particular reference to FIG. 2, it can be seen that needle insertion assembly 14 includes an elongated, advantageously cylindrical, outer needle guard housing 30; an elongated, advantageously cylindrical inner needle support chamber or housing 32 telescopingly received in guard housing 30; and a needle 34 having a shaft portion 35 supported by support housing 32 and extending distally therefrom to a sharp, beveled distal tip 36. Guard housing 30 has a sidewall 40 extending between distal end or cap 42 and proximal end 43 and defining therebetween a space 41 through which support housing 32 moves and into which needle 34 is ultimately received to be enclosed as will be described below.

Figure 3:
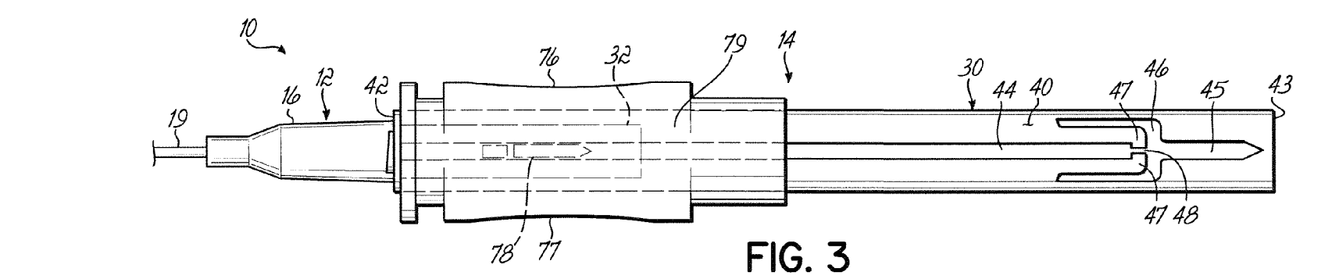
FIG. 3 is a partial, bottom plan view of the catheter insertion device of FIG. 1 in the ready state.

As seen, for example, in FIG. 3, guard housing 30 includes a longitudinal notch 44 running through sidewall 40 along a portion of its length between ends 42 and 43. The proximal end 45 of notch 44 defines a receiving area for purposes to be described. Distal of receiving area 45 is a U-shaped slot detent cutout or notch 46 which defines a pair of fingers 47, the fingers defining a slot 48 therebetween. Fingers 47 are each adapted to cam or be urged away from each other to widen slot 48 for purposes to be described.

Figure 5:
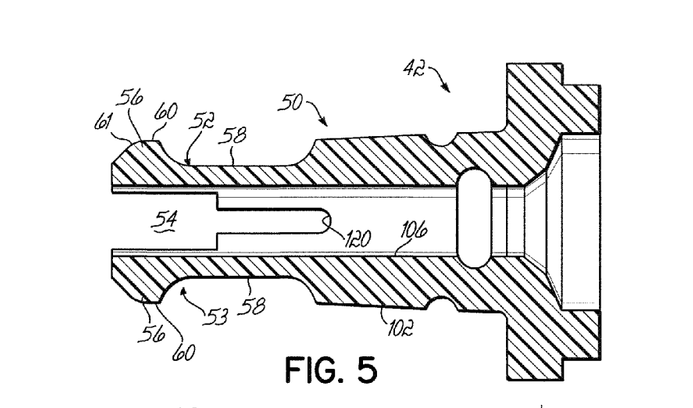
FIG. 5 is a cross-section view of the distal cap or nose of the guard housing of the catheter insertion device of FIG. 1.

As seen in further detail in FIG. 5, distal cap 42 includes a nose 50 sized to be removably fitted within the interior 24 of catheter hub 16 in close proximity with inner wall 23 thereof. Extending from, and in the embodiment of the Figures forming part of, nose 50 is a pair of cooperating members in the form of arms 52, 53 defining a split cylinder also sized to fit within hub 16. Arms 52, 53 are adapted to compress or flex radially toward each other but in the uncompressed, normal state, define a passageway 54 therebetween sized to normally slidably receive needle 34 therethrough. The end of each arm 52, 53 (or at least one of them) includes a holding portion in the form of a detent 56 defining a recess 58 or thinned portion of arm 52 or 53 therebehind. Detent(s) 56 give the respective arms 52, 53 the appearance of a duckbill, and in the uncompressed state, define at their outer periphery 60 an annular ring having a duckbill diameter D2 that is at least slightly larger than catheter hub inner diameter D1 for purposes to be explained. Detents 56 may be distally chamfered as at 61. Advantageously, the recess(es) 58 define an area into which rib 25 is removably received without compressing, or only slightly compressing, the arm(s) 52, 53. The interaction of arms 52, 53, and especially the holding portions 56 thereof, and rib 25 to define a duckbill release mechanism as will be described in greater detail below.

Referring again to FIG. 2, support housing 32 has a sidewall 65 extending between distal end 66 and proximal end 67 and defining therebetween a fluid path or lumen 68. Needle 34 is supported by, and may advantageously be affixed to, support housing 32 such that the shaft 35 thereof extends distally from distal end 66. The fluid path 68 of support housing 32 is in fluid communication with the lumen (not shown) of needle 34 such that blood (not shown) may flash back through needle 34 into the fluid path 68 whereby housing 32 also serves as a flash chamber. To prevent blood (not shown) from exiting support housing 32 during flashback, a plug of venting material 70 adapted to pass air but not blood or other fluids is advantageously fitted into proximal end 67.

Figure 1:
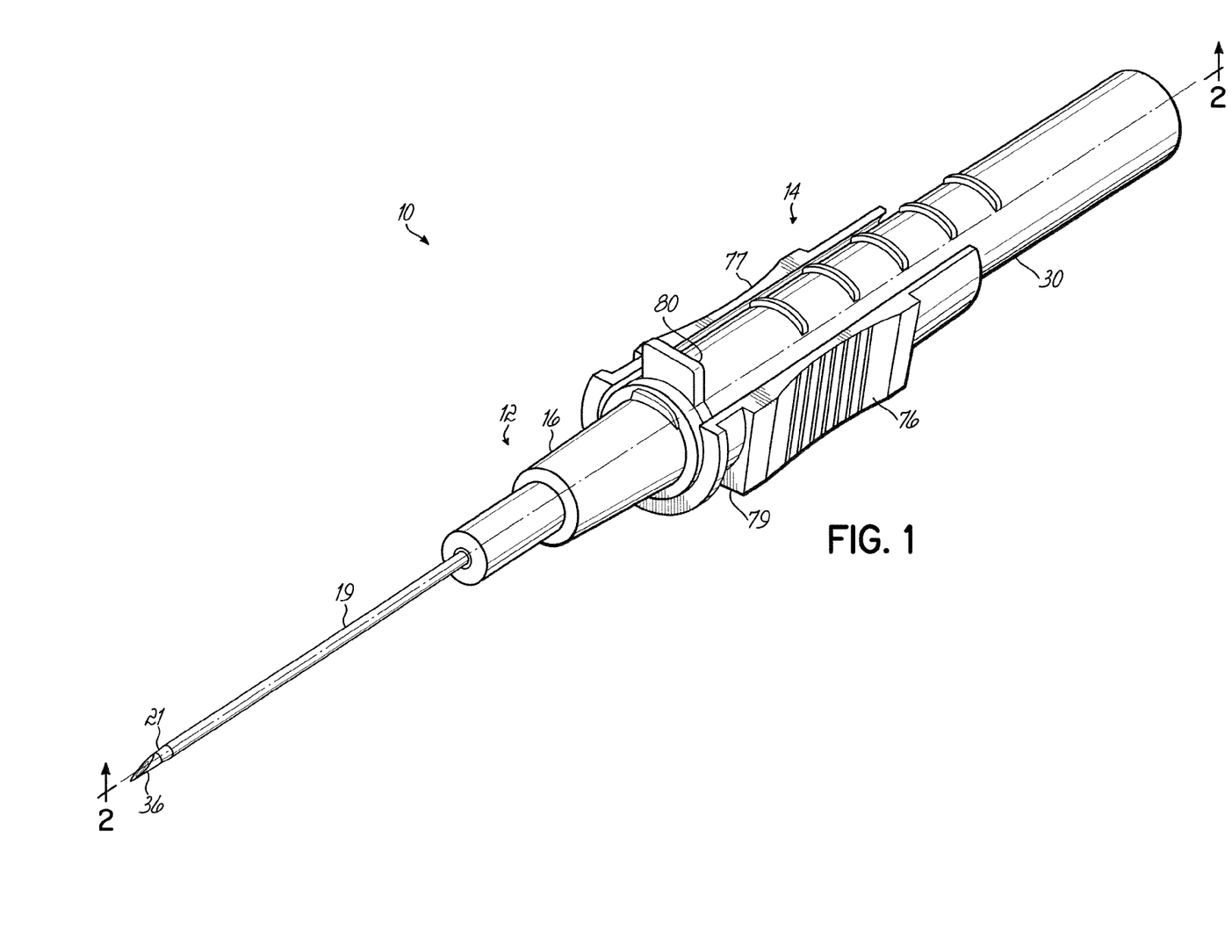
FIG. 1 is a perspective view of an enclosed needle catheter insertion device in the ready state and having a duckbill catheter hub release mechanism in accordance with the principles of the present invention.

Support housing 32 and guard housing 30 are telescopingly received such that one may move relative to the other along a common axis 72. In that regard, support housing 32 has a first or ready position with needle 34 extending through and beyond passageway 54 (FIG. 5) so as to expose sharp tip 36 from catheter tube 19 as seen in FIGS. 1 and 2. In the ready position, guard housing 30 is held to catheter hub 16 by interaction of the holding portions 56 and radially projecting surface 26. More particularly, needle shaft 35 is in passageway 54 between cooperating members 52, 53 thus limiting the ability of either or both of cooperating members 52, 53 to compress (i.e., flex radially inwardly). At the same time, because duckbill diameter D2 is slightly larger than catheter hub inner diameter D1, a generally rigid hold is provided defining the relatively high catheter separation force required to disconnect the components. Further, detents 56 are advantageously seated past rib 25 with a light frictional fit that desirably allows the healthcare user (not shown) to rotate catheter hub 16 relative to needle insertion assembly 14.

Figure 6A:
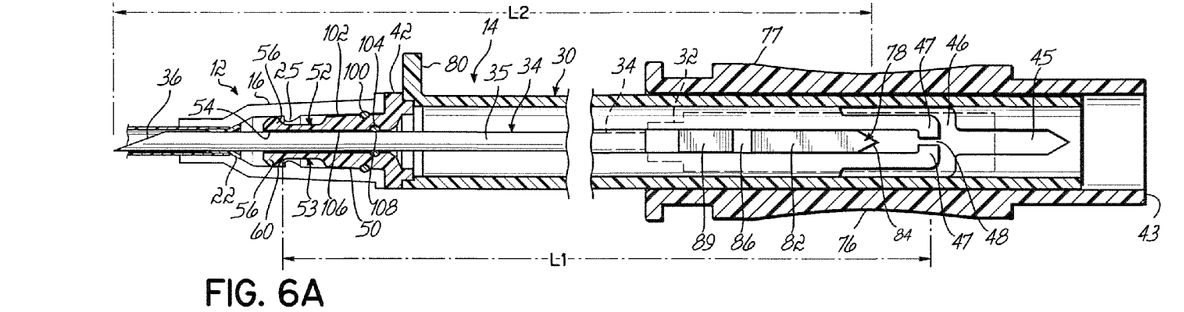
FIGS. 6A though 6E are partial, cross-section views of the catheter insertion device of FIG. 1 showing progression of the needle, needle support housing, and guard housing from the ready state to the shielded state for purposes of explaining the principles of the present invention, with the distal portion of the device being rotated 90° relative to the proximal portion thereof to facilitate the explanation.
Figure 6B:
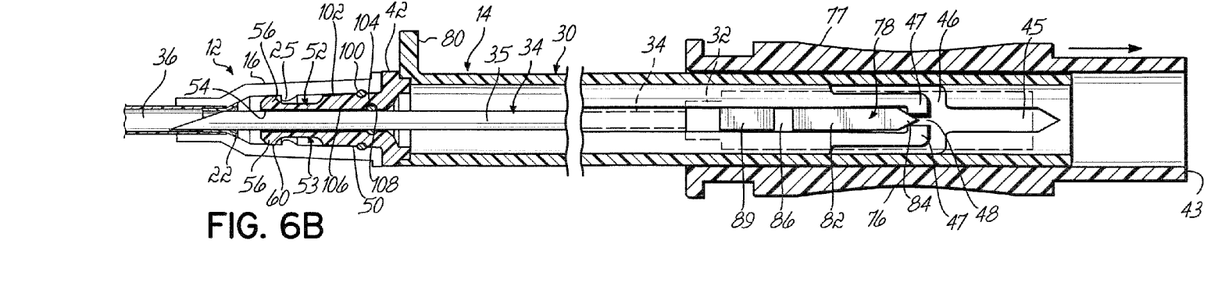
Figure 6C:
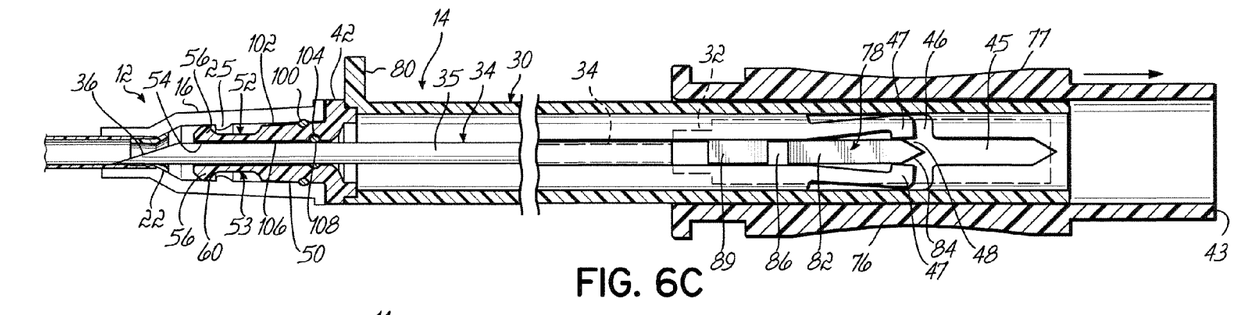
Figure 6D:
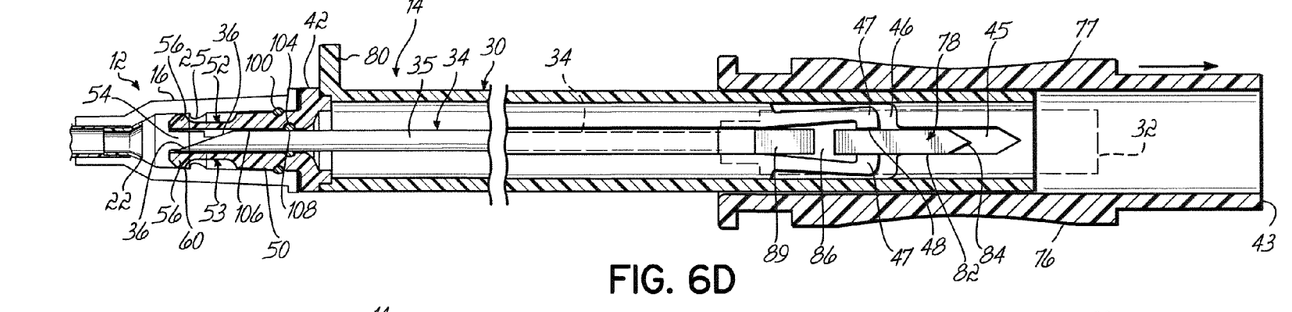
Figure 6E:
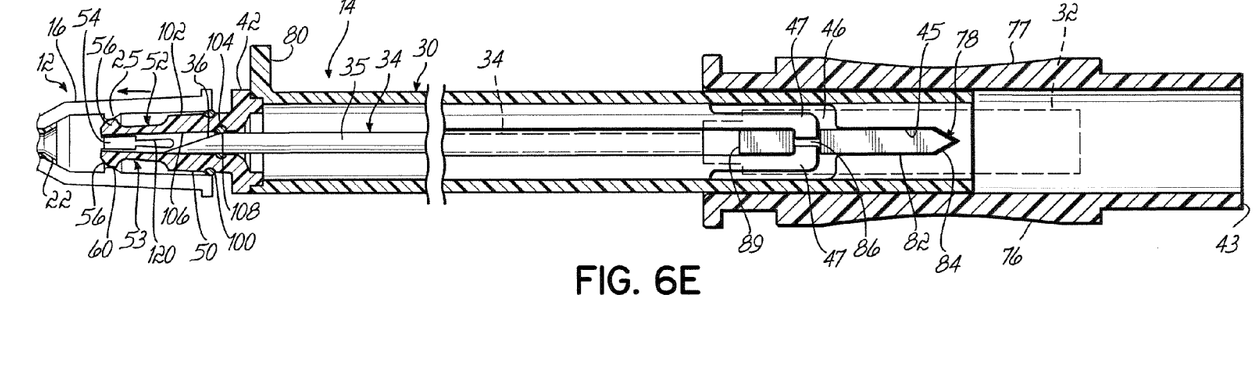
Figure 7:
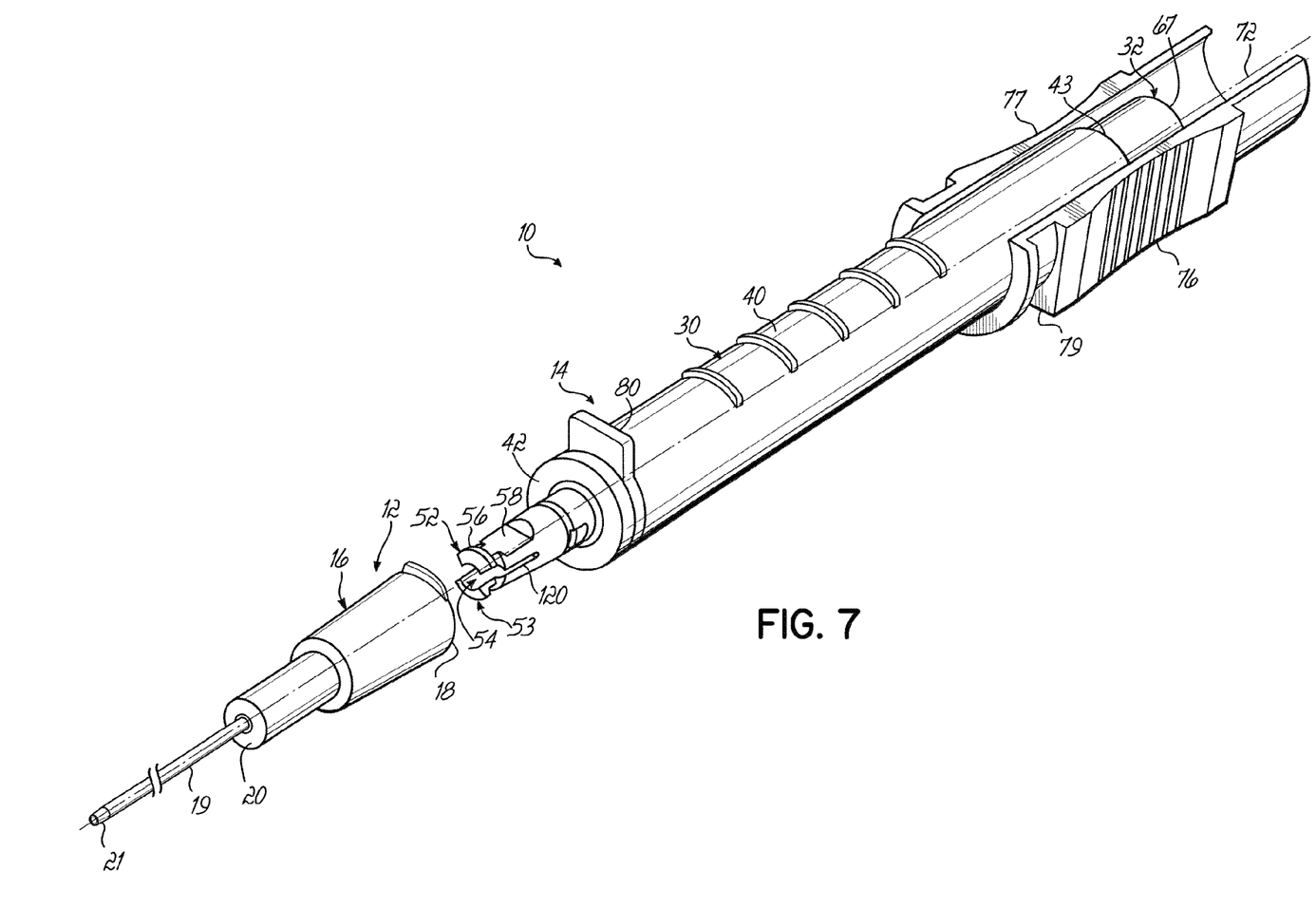
FIG. 7 is a perspective view of the catheter insertion device of FIG. 1 in the shielded state with the needle guard separated from the catheter after the progression of FIGS. 6A through 6E.

Support housing 32 is axially movable to a second or shielded position with needle 34 substantially enclosed by guard housing 30 as seen in FIGS. 6E and 7. In that shielded position, needle 34 is no longer in passageway 54 between arms 52, 53 such that arms 52, 53 flex easily against surface 26. The force required to flex arms 52, 53 is quite low, defining the catheter release force, which is easily overcome to disconnect needle insertion assembly 14 from hub 16. In particular, in the shielded state, detents 56 easily flex against surface 26 (as exemplified in FIG. 6E) and then flex or uncompress back toward the nominal state after passing rib 25 (as exemplified in FIG. 7). Advantageously, proximal portion 27 of hub inner wall 23 has a minimum inner diameter generally not less than duckbill outer diameter D2.

To facilitate moving support housing 32 from the ready position to the shielded position, a pair of gripping wings 76, 77 are positioned adjacent but outside of guard housing sidewall 40. A projection or rib 78 (FIGS. 3 and 6A, for example) extends through longitudinal notch 44 and joins plate 79 supporting gripping wings 76, 77 to sidewall 65 of support housing 32. A medical practitioner may pull on gripping wings 76, 77 (or push against wings 76, 77 by leveraging against push tab 80 of guard housing 30 at its distal end 42) to cause relative motion between housings 30 and 32 from the ready position to the shielded position. The wings 76, 77 may also be joined across the top to, in effect, create a tubular member (not shown) about guard housing 30. The tubular member may be elongated (either as one cylinder or by addition of a cap portion, for example) to match the length of guard housing 30.

Rib 78 is advantageously shaped so that elongated proximal portion 82 defines a slide wall, terminating proximally in a ramp or camming surface 84. A receiver gap 86 is formed in rib 78 distal of slide wall 82 leaving distal rib piece 89. Slot 48 defined by fingers 47 is normally narrower than the width of rib 78. As support housing 32 is moved toward the shielded position, rib 78 and particularly ramp 84 thereof engages fingers 47 and begins to urge them apart so as to widen slot 48 for passage of rib 78 therethrough. As the fingers are being urged apart, the needle support 32 can be said to have moved into a lock actuation stage. In the lock actuation stage, the forces generated by the camming action of ramp 84 against fingers 47 exerts an increased resistance to movement of needle support 32. The foregoing is shown visually in FIGS. 6B (entry into the lock actuation stage) and 6C (passing through the lock actuation stage).

After fingers 47 are urged apart sufficiently for rib 78 to pass into slot 48, the forces generated thereat drop off with continued movement of needle support 32 towards the shielded state as now the only force to contend with is the sliding action of the fingers 47 along the slide wall 82 of rib 78 which is exemplified by FIG. 6D. Continued movement of needle support 32 into the shielded state brings receiver gap 86 into alignment with fingers 47 such that they flex or snap back towards their original state, and into gap 86 behind slide wall 82 as exemplified in FIG. 6E. The foregoing movements also bring the slide wall 82 and associated ramp 84 into receiving area 45. Ramp 84 can abut the proximal-most end of receiving area 75 to prevent any further proximal movement of needle support 32 relative to guard housing 30. Also, with fingers 47 snapped back about slide wall 82 and into gap 86, needle support 32 is locked in the shielded state such that needle 34 can not be readily pushed back out of guard housing 30. It is thus seen that fingers 47 and rib 78, or at least portions thereof, define cooperating lock elements to lock needle support 32 in the shielded position. It will also be recognized that, in the locked state, interaction of the surfaces of the cooperating lock elements creates a situation where extremely high forces can be applied in a proximal direction on housings 30 and/or 32 and away from catheter 12 to facilitate disconnection of insertion device 14 from catheter 12 with needle 34 shielded by guard housing 30, at which time essentially only the relatively low catheter release force need be overcome.

In order to provide a reliable disconnection, it is desired that the forces created upon entry into the lock actuation stage not be so great as to overcome the forces needed to maintain the hold of guard housing 30 to catheter hub 16. To that end, and in accordance with the principles of the present invention, the cooperating lock elements are positioned to take advantage of the high catheter separation force due to the presence of needle 34 in the passageway 54 between arms 52, 53 during the increased resistance to movement of needle support 32 encountered as needle support 32 moves into the lock actuation stage. Thus, in the enclosed needle catheter insertion device 10 shown herein, fingers 47 and ramp 84 are positioned away from the duckbill release mechanism such that ramp 84 begins to engage fingers 47 while needle 34 is still in passageway 54 as seen in FIG. 6B. More particularly, and as seen in FIG. 6A, the fingers 47 are positioned to define slot 48 spaced a first distance L1 measured through passageway 54 and guard housing 30 from holding portion(s) 60, and ramp 84 is positioned to be spaced a second distance L2 measured through the needle 34 from the sharp tip 36 thereof, with the second distance L2 being greater than the first distance L1. As a consequence, increased resistance to movement of needle support 32 is encountered while the hold between catheter hub 16 and guard housing 30 is at its highest.

Continued proximal movement of needle support housing 32 relative to guard housing 30 continues through the lock actuation stage (FIG. 6C) whereat the forces required to fully flex fingers 47 are at their highest, all the while the hold between catheter hub 16 and cooperating members 52, 53 is also at its highest due to the catheter separation force. It is advantageous to minimize the force required to flex fingers 47, such as by minimizing the cross-sectional area thereof which may be by making fingers 47 thinner or narrower. To that end, in the embodiment shown herein, the width of fingers 47 is reduced by about twenty thousandths as compared to a standard PROTECTIV Safety I.V. Catheter. As the lock actuation stage is completed, needle support 32 moves into a slide stage (FIG. 6D) whereat fingers 47 are now bearing against slide wall 82. In that slide stage, there is no need for further flexure of fingers 47. Instead, the forces relax and involve a lower level of resistance to movement of needle support 32. That lower level of resistance is advantageously employed to provide lower forces as needle 34 starts to come within passageway 54 whereat the force relationship between catheter hub 16 and members 52, 53 begins to move from the high forces involved for catheter separation force requirement, to the much lower forces necessary to overcome the catheter release force. Slide wall 82 could even be tapered distally (not shown) to thereby reduce its width and further lower the forces acting between fingers 47 and slide wall 82 during the slide stage.

In the final movement of needle support 32 into the shielded position, fingers 47 snap into receiver gap 86 whereat substantial forces can be applied without the cooperating lock elements coming apart. In that stage, needle support 32 is in the shielded position, and needle 34 is out from between members 52, 53. The forces holding housings 30 and 32 locked in the shielded position are quite high, whereas the catheter release force is quite low such that the holding portions 60 of members 52, 53 readily and easily flex against projecting surface(s) 26 as guard 30 begins to pull away from catheter hub 16 as exemplified in FIG. 6E. Continued pulling of needle support 32 and/or guard housing 30 easily removes insertion device 14 from catheter 12 so that they are now disconnected as seen in FIG. 7. With the components disconnected, hub 16 is exposed for use by the medical practitioner, with needle insertion assembly 14 locked in the shielded position ready to be discarded.

Nose 50 advantageously includes one or more internal or external seals such as co-molded elastomeric gasket 100 integrally associated with exterior wall 102 of nose 50 to form a seal with the inner wall 23 of catheter hub 16 and/or co-molded elastomeric gasket 104 integrally associated with inner wall 106 of nose 50 defining proximal passageway 108 through which needle 34 is received to form a seal therewith as shown herein and as more particularly shown and described in the concurrently filed No. MDXVA-104US, the disclosure of which is incorporated herein by reference as if fully set out herein.

The size of the passageway 54 may be closely dimensioned to the diameter of needle shaft 35 so that passageway 54 is largely taken up by the presence of needle shaft 35. Compression or other inward flexing of the cooperating members 52, 53 is thus limited, thereby restricting release of cooperating members 52, 53 from catheter hub 16. Tolerance of the gap between the relative inner diameter of passageway 54 of cooperating members 52, 53 and the outside diameter of needle shaft 35 may be selected to reduce the likelihood of removal of the duckbills 52, 53 from catheter hub 16 when needle 34 is present. Further, with needle shaft 35 out from within passageway 54, duckbills 52, 53 may be easily loaded into catheter hub 16 by pushing them into hub 16 (or pushing hub 16 over arms 52, 53) such that detents 56 impact against rib 25 to cause the cooperating members 52, 53 to flex slightly until detents 56 are distally beyond rib 25 at which time they flex back out to lightly hold to catheter hub 16. Needle shaft 35 may then be loaded to resist inward flexing of members 52, 53 greatly increasing the holding force. Alternatively, with shaft 35 in place, duckbills 52, 53 could be forced into hub 16. Chamfers 61 may help with such loading.

Members 52, 53 are shown defining a split cylinder. The forces required to flex arms 52, 53 are defined in part by the thickness of the plastic at detents 56 and/or recesses 58. Further adjustment is provided by the depth of the notches 120 formed in nose 50 (FIG. 5), while arms 52, 53 could be arcuate in cross-section, they could instead be half-moon in cross-section. Further, each arm 52, 53 could be provided with an internal, depending longitudinal ridge (not shown) to define, in effect, the inner diametrical size of passageway 54 as described in U.S. patent application Ser. No. 11/161,554 filed Aug. 8, 2005, the disclosure of which is incorporated herein by reference. Cooperating members 52, 53 may be upper and lower segments of a split cylinder, or may define respective large and small aspects and/or side to side segments of a split cylinder. Moreover, while they are both described as being able to flex and with detents at their distal ends, it will be recognized by those of skill in the art that in only one of the members may be resilient enough to easily flex, only one member may include a detent, and/or the detent(s) may be away from the distal end(s). Also, while rib 25 (and thus surface 26) is shown as being generally continuous, it may have one or more gaps (not shown). Advantageously, any such gap(s), if provided, would each be smaller than a circumferential width of the detent 56.

In use of enclosed needle catheter insertion device 10, any protective sheath (not shown) is removed, and with device 10 in the ready position, needle tip 36 inserted into a patient (not shown) to position catheter tube 19 as desired, including by rotation of catheter hub 16 relative to needle insertion assembly 14, if needed. Once tube 19 is positioned as desired, needle support housing 32 is moved proximally within guard housing 30 into the lock actuation stage with the needle 34 still in passageway 54. Increased resistance to movement of needle support 32 is not enough to overcome the catheter separation force. Needle support 32 is continued in its movement through a slide stage whereat there is reduced resistance of movement of needle support 32. Continued movement brings needle support 32 into the shielded state whereat it is locked. In the shielded state, the forces to overcome the lock are very high, whereas, because needle 34 is no longer in passageway 54 between arms 52, 53, the catheter release force is quite low. Arms 52, 53 thus flex against rib 25 allowing needle insertion assembly 14 to disconnect from catheter hub 16.

While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. For example, while surface 26 has been described as a distal-directed aspect of radially inwardly projecting rib 25, the surface could, alternatively, be defined as a proximal aspect of a radially outwardly projecting groove (or grooves). Further, while the lock elements are shown as having two fingers 47, operation is possible with only one flexing finger 47. Further, while needle support 32 is shown as being sized so as to be completely within guard housing 30 in the ready position, support housing 32 could be elongated (not shown) so as to provide fluid path access as shown and describe din commonly assigned and concurrently filed U.S. patent application entitled "Enclosed Needle Device with Fluid Path Access", the disclosure of which is incorporated herein by reference in its entirety. The invention in its broader aspects is therefore not limited to the specific details, representative apparatus and method, and illustrated examples shown and described. Accordingly, departures may be made from such details without departing from the scope or spirit of Applicant's general inventive concept.

Having described the invention what is claimed is:

1. A safety catheter device comprising:
a catheter including a catheter hub having an interior radially inwardly projecting rib, and a catheter tube extending from the catheter hub distal end; and
an enclosed needle guard removably coupled to the catheter hub including: a needle support with a needle extending therefrom; a guard housing movably receiving the needle support and having a pair of cooperating members extending from an end thereof and sized to fit within the catheter hub, the members having a normally uncompressed position defining a passageway therebetween sized to freely receive the needle therethrough, at least one member including a holding portion adapted to cooperate with the catheter hub radially projecting surface to releasably hold the guard housing to the catheter hub such that the holding portion releases from the radially projecting surface by compression of the member to narrow the passageway, wherein presence of the needle in the passageway substantially limits such compression to thereby restrict release of the guard housing from the catheter hub, the needle support being movable from a ready position with the needle extending through and beyond the passageway so as to expose a sharp tip of the needle from the catheter tube to a shielded position with the needle substantially enclosed by the guard housing, the needle support being movable into a lock actuation stage with the needle in the passageway prior to moving into the shielded position; and cooperating lock elements on the needle support and guard housing locking the needle support in the shielded position, the needle support being movable from the ready position toward the lock actuation stage with the cooperating lock elements exerting increased resistance to movement of the needle support as it enters the lock actuation stage.

2. The safety catheter of claim 1, the guard housing being elongated, the needle support being axially movable from the ready position, into the lock actuation stage, and into the shielded position.

3. The safety catheter of claim 1, the cooperating lock elements adapted to generate forces on entry into the lock actuation stage less than the force required to substantially compress the member with the needle in the passageway.

4. The safety catheter of claim 1, the cooperating lock element on the guard housing being spaced a first distance measured through the passageway and guard housing from the holding portion, the cooperating lock element on the needle support being spaced a second distance measured through the needle from the sharp tip of the needle, the second distance being greater than the first distance.

5. The safety catheter of claim 1, each member including a holding portion adapted to cooperate with the radially inwardly projecting rib of the catheter hub and being compressible upon deflection of its holding portion to narrow the passageway.

6. The safety catheter of claim 1, the holding portion being on a free end of the member.

7. The safety catheter of claim 1 the rib being continuous.

8. The safety catheter of claim 1 wherein the needle has an elongated shaft of a predetermined diameter, the size of the passageway being closely dimensioned to the diameter of the needle shaft.

9. The safety catheter of claim 1, the needle support being movable from the lock actuation stage through a slide stage as the needle moves through the passageway, the cooperating lock elements exerting reduced resistance to movement of the needle support through the slide stage.

10. The safety catheter of claim 9, the guard housing being elongated, the needle support being axially movable from the ready position, into the lock actuation stage, through the slide stage, and into the shielded position.

11. The safety catheter of claim 1, the cooperating members being received into the catheter hub through an open mouth thereof, the catheter hub having an interior surface portion extending along a taper between the open mouth and the radially inwardly projecting rib.

12. The safety catheter of claim 11, the tapered interior surface portion having a minimum inner diameter generally not less than a maximum outer diameter of the cooperating members defined at the holding portion.

13. The safety catheter of claim 1, the cooperating lock elements including a lock finger defining a slot and a lock ramp, the lock ramp adapted to urge the lock finger so as to widen the slot as the needle support enters the lock actuation stage.

14. The safety catheter of claim 13, the cooperating lock elements further including cooperating surfaces adapted to hold the needle support against movement out of the shielded position.

15. The safety catheter of claim 13, the lock ramp being on the needle support and the lock finger being on the guard housing.

16. The safety catheter of claim 13 further comprising a slide wall extending from the lock ramp and passing along the lock finger as the needle support moves through the lock actuation stage.

17. The safety catheter of claim 7, the lock ramp being defined on the slide wall.

18. A safety catheter device comprising:

a catheter including a catheter hub having an interior radially inwardly projecting rib, and a catheter tube extending from the catheter hub distal end; and an enclosed needle guard removably coupled to the catheter hub including: a needle support with a needle extending therefrom; a guard housing movably receiving the needle support and having a pair of cooperating members extending from an end thereof and sized to fit within the catheter hub, the members having a normally uncompressed position defining a passageway therebetween sized to freely receive the needle therethrough, at least one member including a holding portion adapted to cooperate with the catheter hub radially projecting surface to releasably hold the guard housing to the catheter hub such that the holding portion releases from the radially projecting surface by compression of the member to row the passageway, wherein presence of the needle in the passageway substantially limits such compression to thereby restrict release of the guard housing from the catheter hub, the needle support including a projection extending therefrom through a notch in the guard housing and being movable from a ready position with the needle extending through and beyond the passageway so as to expose a sharp tip of the needle from the catheter tube to a shielded position with the needle substantially enclosed by the guard housing, the needle support being movable into a lock actuation stage with the needle in the passageway prior to moving into the shielded position; and cooperating lock elements on the needle support and guard housing locking the needle support in the shielded position, one of the cooperating lock elements being associated with the projection, the needle support being movable from the ready position toward the lock actuation stage with the cooperating lock elements exerting increased resistance to movement of the needle support as it enters the lock actuation stage.

19. The safety catheter of claim 18, the guard housing being elongated, the needle support being axially movable from the ready position, into the lock actuation position, and into the shielded position.

20. The safety catheter of claim 18, the cooperating lock elements adapted to generate forces on entry into the lock actuation stage less than the force required to substantially compress the member with the needle in the passageway.

21. The safety catheter of claim 18, the rib being continuous.

22. The safety catheter of claim 18, the lock ramp being on the needle support and the lock finger being on the guard housing.

23. The safety catheter of claim 18, the cooperating lock element on the guard housing being spaced a first distance measured through the passageway and guard housing from the holding portion, the cooperating lock element on the needle support being spaced a second distance measured through the needle from the sharp tip of the needle, the second distance being greater than the first distance.

24. The safety catheter of claim 18, each member having a holding portion adapted to cooperate with the radially inwardly directed rib of the catheter hub and being compressible upon deflection of its holding portion to narrow the passageway.

25. The safety catheter of claim 18, the holding portion being on a free end of the member.

26. The safety catheter of claim 18 wherein the needle has an elongated shaft of a predetermined diameter, the size of the passageway being closely dimensioned to the diameter of the needle shaft.

27. The safety catheter of claim 18, the needle support being movable from the lock actuation stage through a slide stage as the needle moves through the passageway, the cooperating lock elements exerting reduced resistance to movement of the needle support through the slide stage.

28. The safety catheter of claim 27, the guard housing being elongated, the needle support being axially movable from the ready position, into the lock actuation stage, through the slide stage, and into the shielded position.

29. The safety catheter of claim 18, the cooperating members being received into the catheter hub through an open mouth thereof, the catheter hub having an interior surface portion extending along a taper between the open mouth and the radially inwardly projecting fib.

30. The safety catheter of claim 29, the tapered interior surface portion having a minimum inner diameter generally not less than a maximum outer diameter of the cooperating members defined at the holding portion.

31. The safety catheter of claim 18, the cooperating lock elements including a lock finger defining a slot and a lock ramp, the lock ramp adapted to urge the lock finger so as to widen the slot as the needle support enters the lock actuation stage.

32. The safety catheter of claim 31, the cooperating lock elements further including cooperating surfaces to hold the needle support against movement out of the shielded position.

33. The safety catheter of claim 31 further comprising a slide wall extending from the lock ramp and passing along the lock finger as the needle support moves through the lock actuation stage.

34. The safety catheter of claim 33, the lock ramp being defined on the slide wall.

* * * * *

UNITED STATES PATENT AND TRADEMARK OFFICE
CERTIFICATE OF CORRECTION

| | | |
|---|---|---|
| PATENT NO. | : 7,658,725 B2 | Page 1 of 1 |
| APPLICATION NO. | : 11/276152 | |
| DATED | : February 9, 2010 | |
| INVENTOR(S) | : Dennis M. Bialecki et al. | |

It is certified that error appears in the above-identified patent and that said Letters Patent is hereby corrected as shown below:

Claim 17
Column 11, line 5, "The safety catheter of claim 7" should be -- the safety catheter of claim 16 --

Claim 18
Column 11, line 24, "row the passageway" should be -- narrow the passageway --

Claim 29
Column 12, line 35, "projecting fib" should be -- projecting rib --

Signed and Sealed this

Eighteenth Day of January, 2011

David J. Kappos
*Director of the United States Patent and Trademark Office*